United States Patent
McDonald et al.

(10) Patent No.: US 8,818,526 B2
(45) Date of Patent: *Aug. 26, 2014

(54) SYSTEMS AND METHODS FOR ALTERING ONE OR MORE RF-RESPONSE PROPERTIES OF ELECTRICAL STIMULATION SYSTEMS

(71) Applicant: Boston Scientific Neuromodulation Corporation, Valencia, CA (US)

(72) Inventors: Matthew Lee McDonald, Pasadena, CA (US); Ross Daniel Venook, Millbrae, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/769,002

(22) Filed: Feb. 15, 2013

(65) Prior Publication Data
US 2013/0158642 A1  Jun. 20, 2013

Related U.S. Application Data

(63) Continuation of application No. 12/544,903, filed on Aug. 20, 2009, now Pat. No. 8,380,324.

(51) Int. Cl.
*A61N 1/08* (2006.01)
*A61N 1/05* (2006.01)

(52) U.S. Cl.
CPC ............ *A61N 1/05* (2013.01); *A61N 2001/086* (2013.01); *H01R 2201/12* (2013.01); *A61N 1/056* (2013.01)
USPC ............................................ 607/116; 607/63

(58) Field of Classification Search
CPC .......................... A61N 1/05; A61N 2001/086
USPC .................. 607/63, 115–117, 119, 121, 122; 600/372–374, 377, 378
See application file for complete search history.

(56) References Cited

U.S. PATENT DOCUMENTS 4,146,036 A * 3/1979 Dutcher et al. ............... 607/127
5,217,010 A    6/1993 Tsitlik et al.
(Continued)

FOREIGN PATENT DOCUMENTS

| EP | 2067501 A2 | 6/2009 |
|---|---|---|
| WO | 02065895 A2 | 8/2002 |

(Continued)

OTHER PUBLICATIONS

U.S. Appl. No. 12/544,903, Official Communication mailed Jul. 15, 2011.

(Continued)

*Primary Examiner* — Carl H Layno
*Assistant Examiner* — Eugene Wu
(74) *Attorney, Agent, or Firm* — Lowe Graham Jones PLLC; Patrick R. Turner

(57) ABSTRACT

An implantable lead includes a lead body and at least one safety element. The lead body has a distal end and a proximal end. The lead body defines at least one lumen extending along at least a portion of the lead body. The lead body includes a plurality of electrodes disposed on the distal end of the lead body, a plurality of terminals disposed on the proximal end of the lead body, and a plurality of conductors disposed in the lead body, each conductor electrically coupling at least one of the electrodes to at least one of the terminals. The at least one safety element is disposed along at least a portion of the lead body and is configured and arranged to reduce damage to patient tissue adjacent to the plurality of electrodes due to heating, induced electrical signals, or both when the lead is exposed to radio frequency irradiation.

18 Claims, 8 Drawing Sheets

(56) References Cited

U.S. PATENT DOCUMENTS

| | | | |
|---|---|---|---|
| 5,366,496 A | 11/1994 | Dahl et al. | |
| 5,688,267 A | 11/1997 | Panescu et al. | |
| 5,796,044 A * | 8/1998 | Cobian et al. | 174/103 |
| 5,876,422 A * | 3/1999 | van Groeningen | 607/3 |
| 6,181,969 B1 | 1/2001 | Gord | |
| 6,516,227 B1 | 2/2003 | Meadows et al. | |
| 6,609,032 B1 | 8/2003 | Woods et al. | |
| 6,718,203 B2 | 4/2004 | Weiner et al. | |
| 6,718,207 B2 | 4/2004 | Connelly | |
| 6,725,092 B2 | 4/2004 | MacDonald et al. | |
| 6,741,892 B1 | 5/2004 | Meadows et al. | |
| 6,746,474 B2 | 6/2004 | Saadat | |
| 6,757,566 B2 | 6/2004 | Weiner et al. | |
| 6,760,628 B2 | 7/2004 | Weiner et al. | |
| 6,763,268 B2 | 7/2004 | MacDonald et al. | |
| 6,778,856 B2 | 8/2004 | Connelly et al. | |
| 6,795,736 B2 | 9/2004 | Connelly et al. | |
| 6,799,069 B2 | 9/2004 | Weiner et al. | |
| 6,819,954 B2 | 11/2004 | Connelly | |
| 6,819,958 B2 | 11/2004 | Weiner et al. | |
| 6,829,509 B1 | 12/2004 | MacDonald et al. | |
| 6,845,266 B2 | 1/2005 | Weiner et al. | |
| 6,850,805 B2 | 2/2005 | Connelly et al. | |
| 6,871,091 B2 | 3/2005 | Wilkinson et al. | |
| 6,875,180 B2 | 4/2005 | Weiner et al. | |
| 6,901,290 B2 | 5/2005 | Foster et al. | |
| 6,901,292 B2 | 5/2005 | Hrdlicka et al. | |
| 6,944,489 B2 | 9/2005 | Zeijlemaker et al. | |
| 6,954,674 B2 | 10/2005 | Connelly | |
| 6,985,775 B2 | 1/2006 | Reinke et al. | |
| 6,993,387 B2 | 1/2006 | Connelly et al. | |
| 7,010,357 B2 | 3/2006 | Helfer et al. | |
| 7,013,174 B2 | 3/2006 | Connelly et al. | |
| 7,047,074 B2 | 5/2006 | Connelly et al. | |
| 7,127,294 B1 * | 10/2006 | Wang et al. | 607/36 |
| 7,164,950 B2 | 1/2007 | Kroll et al. | |
| 7,174,219 B2 | 2/2007 | Wahlstrand et al. | |
| 7,306,621 B1 * | 12/2007 | Halla et al. | 607/113 |
| 7,761,165 B1 | 7/2010 | He et al. | |
| 8,380,324 B2 * | 2/2013 | McDonald et al. | 607/116 |
| 8,406,895 B2 * | 3/2013 | Erbstoeszer et al. | 607/115 |
| 2002/0128689 A1 | 9/2002 | Connelly et al. | |
| 2002/0128691 A1 | 9/2002 | Connelly | |
| 2002/0133086 A1 | 9/2002 | Connelly et al. | |
| 2002/0133199 A1 | 9/2002 | MacDonald et al. | |
| 2002/0133200 A1 | 9/2002 | Weiner et al. | |
| 2002/0133201 A1 | 9/2002 | Connelly et al. | |
| 2002/0133202 A1 | 9/2002 | Connelly et al. | |
| 2002/0133208 A1 | 9/2002 | Connelly | |
| 2002/0133211 A1 | 9/2002 | Weiner et al. | |
| 2002/0133216 A1 | 9/2002 | Connelly et al. | |
| 2002/0138102 A1 | 9/2002 | Weiner et al. | |
| 2002/0138107 A1 | 9/2002 | Weiner et al. | |
| 2002/0138108 A1 | 9/2002 | Weiner et al. | |
| 2002/0138110 A1 | 9/2002 | Connelly et al. | |
| 2002/0138112 A1 | 9/2002 | Connelly et al. | |
| 2002/0138113 A1 | 9/2002 | Connelly et al. | |
| 2002/0138124 A1 | 9/2002 | Helfer et al. | |
| 2002/0143258 A1 | 10/2002 | Weiner et al. | |
| 2002/0147470 A1 | 10/2002 | Weiner et al. | |
| 2002/0183796 A1 | 12/2002 | Connelly | |
| 2002/0198569 A1 | 12/2002 | Foster et al. | |
| 2003/0114905 A1 | 6/2003 | Kuzma | |
| 2004/0059392 A1 | 3/2004 | Parramon et al. | |
| 2005/0090886 A1 | 4/2005 | MacDonald et al. | |
| 2005/0113676 A1 | 5/2005 | Weiner et al. | |
| 2005/0113873 A1 | 5/2005 | Weiner et al. | |
| 2005/0113874 A1 | 5/2005 | Connelly et al. | |
| 2005/0113876 A1 | 5/2005 | Weiner et al. | |
| 2005/0159661 A1 | 7/2005 | Connelly et al. | |
| 2005/0165465 A1 | 7/2005 | Pianca et al. | |
| 2005/0171585 A1 * | 8/2005 | Saadat | 607/96 |
| 2005/0283167 A1 | 12/2005 | Gray | |
| 2005/0283168 A1 | 12/2005 | Gray | |
| 2005/0283213 A1 | 12/2005 | Gray | |
| 2005/0283214 A1 | 12/2005 | Gray | |
| 2005/0288750 A1 | 12/2005 | Gray | |
| 2005/0288751 A1 | 12/2005 | Gray | |
| 2005/0288752 A1 | 12/2005 | Gray | |
| 2005/0288753 A1 | 12/2005 | Gray | |
| 2005/0288754 A1 | 12/2005 | Gray | |
| 2005/0288755 A1 | 12/2005 | Gray | |
| 2005/0288756 A1 | 12/2005 | Gray | |
| 2005/0288757 A1 | 12/2005 | Gray | |
| 2007/0150007 A1 | 6/2007 | Anderson et al. | |
| 2007/0150036 A1 | 6/2007 | Anderson | |
| 2007/0161294 A1 | 7/2007 | Brase et al. | |
| 2007/0168003 A1 | 7/2007 | Gray | |
| 2007/0168005 A1 | 7/2007 | Gray | |
| 2007/0168006 A1 | 7/2007 | Gray | |
| 2007/0173911 A1 | 7/2007 | Gray | |
| 2007/0198073 A1 | 8/2007 | MacDonald et al. | |
| 2007/0219595 A1 | 9/2007 | He | |
| 2007/0239243 A1 | 10/2007 | Moffitt et al. | |
| 2007/0244535 A1 * | 10/2007 | Inman et al. | 607/116 |
| 2008/0058902 A1 | 3/2008 | Gray et al. | |
| 2008/0262584 A1 * | 10/2008 | Bottomley et al. | 607/119 |
| 2009/0259281 A1 * | 10/2009 | Weiss et al. | 607/116 |
| 2010/0217356 A1 * | 8/2010 | Bikson et al. | 607/63 |
| 2011/0046700 A1 * | 2/2011 | McDonald et al. | 607/63 |
| 2012/0203100 A1 * | 8/2012 | Weiss et al. | 600/421 |
| 2013/0158642 A1 * | 6/2013 | McDonald et al. | 607/116 |

FOREIGN PATENT DOCUMENTS

| | | |
|---|---|---|
| WO | 03090846 A2 | 11/2003 |
| WO | 2004095385 A2 | 11/2004 |
| WO | 2005070494 A1 | 8/2005 |
| WO | 2007008301 A2 | 1/2007 |
| WO | 2007118194 A2 | 10/2007 |

OTHER PUBLICATIONS

U.S. Appl. No. 12/544,903, Official Communication mailed Nov. 3, 2011.

U.S. Appl. No. 12/544,903, Official Communication mailed May 31, 2012.

* cited by examiner

SYSTEMS AND METHODS FOR ALTERING ONE OR MORE RF-RESPONSE PROPERTIES OF ELECTRICAL STIMULATION SYSTEMS

CROSS-REFERENCE TO RELATED APPLICATIONS

This patent application is a continuation of U.S. patent application Ser. No. 12/544,903 filed on Aug. 20, 2009 now U.S. Pat. No. 8,380,324, which is incorporated herein by reference.

FIELD

The present invention is directed to the area of implantable electrical stimulation systems and methods of making and using the systems. The present invention is also directed to implantable electrical stimulation systems having leads that include one or more safety elements for altering one or more RF-response properties of the lead, as well as methods of making and using the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Conventional implanted electrical stimulation systems are often incompatible with magnetic resonance imaging ("MRI") due to the large radio frequency ("RF") pulses used during MRI. The RF pulses can generate transient signals in the conductors and electrodes of an implanted lead. These signals can have deleterious effects including, for example, unwanted heating of the tissue causing tissue damage, induced currents in the lead, or premature failure of electronic components.

BRIEF SUMMARY

In one embodiment, an implantable lead includes a lead body and at least one safety element. The lead body has a distal end and a proximal end. The lead body defines at least one lumen extending along at least a portion of the lead body. The lead body includes a plurality of electrodes disposed on the distal end of the lead body, a plurality of terminals disposed on the proximal end of the lead body, and a plurality of conductors disposed in the lead body, each conductor electrically coupling at least one of the electrodes to at least one of the terminals. The at least one safety element is disposed along at least a portion of the lead body and is configured and arranged to reduce damage to patient tissue adjacent to the plurality of electrodes due to heating, induced electrical signals, or both when the lead is exposed to radio frequency irradiation.

In another embodiment, an electrical stimulating system includes a lead, a control module, and a connector for receiving the lead. The lead includes a lead body and at least one safety element. The lead body has a distal end and a proximal end. The lead body defines at least one lumen extending along at least a portion of the lead body. The lead body includes a plurality of electrodes disposed on the distal end of the lead body, a plurality of terminals disposed on the proximal end of the lead body, and a plurality of conductors disposed in the lead body, each conductor electrically coupling at least one of the electrodes to at least one of the terminals. The at least one safety element is disposed along at least a portion of the lead body and is configured and arranged to reduce damage to patient tissue adjacent to the plurality of electrodes due to heating, induced electrical signals, or both when the lead is exposed to radio frequency irradiation. The control module is configured and arranged to electrically couple to the proximal end of the lead body. The control module includes a housing and an electronic subassembly disposed in the housing. The connector has a proximal end, a distal end, and a longitudinal length. The connector is configured and arranged to receive the lead. The connector includes a connector housing defining a port at the distal end of the connector. The port is configured and arranged for receiving the proximal end of the lead body. A plurality of connector contacts are disposed in the connector housing. The connector contacts are configured and arranged to couple to at least one of the plurality of terminals disposed on the proximal end of the lead body.

In yet another embodiment, a method for forming an implantable lead includes disposing an elongated conductor in a lead body of the lead. At least one safety element is disposed in at least one lumen defined along at least a portion of the lead body. The safety element is configured and arranged to reduce damage to patient tissue adjacent to the plurality of electrodes due to heating, induced electrical signals, or both when the lead is exposed to radio frequency irradiation. A first end of the conductor is coupled to an electrode disposed on a distal end of the lead. A second end of the conductor is coupled to a terminal disposed on a proximal end of the lead. The terminal is electrically coupled to a control module configured and arranged to generate electrical signals for stimulating patient tissue via the electrode.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation systems having leads that include one or more safety elements for altering one or more RF-response properties of the lead, as well as methods of making and using the leads and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,672,734; 7,761,165; 7,949,395; 7,974,706; 8,175,710; and 8,364,278; and U.S. Patent Application Publication No. 2007/0150036, all of which are incorporated by reference.

Figure 1:
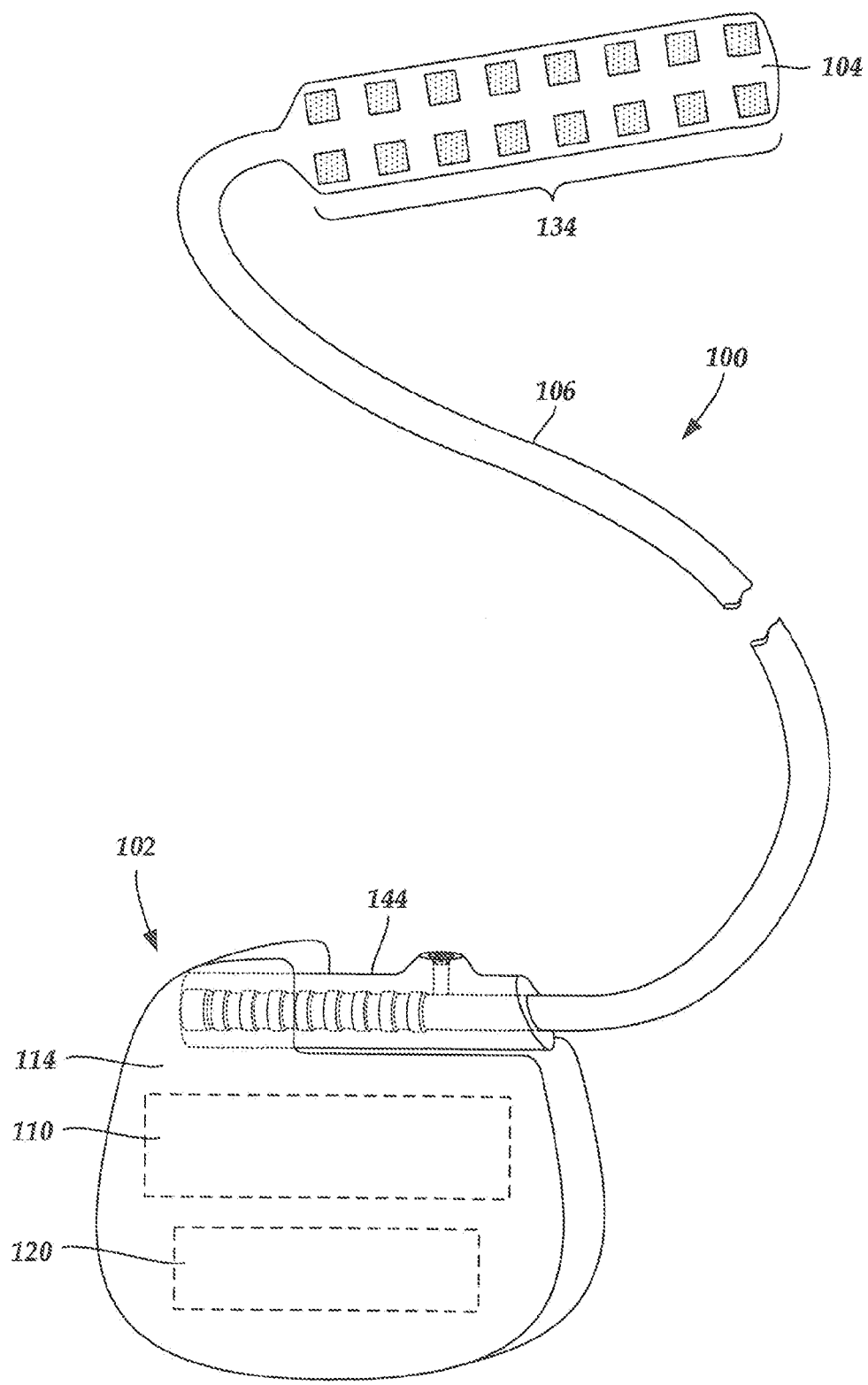
FIG. 1 is a schematic view of one embodiment of an electrical stimulation system, according to the invention.
Figure 2:
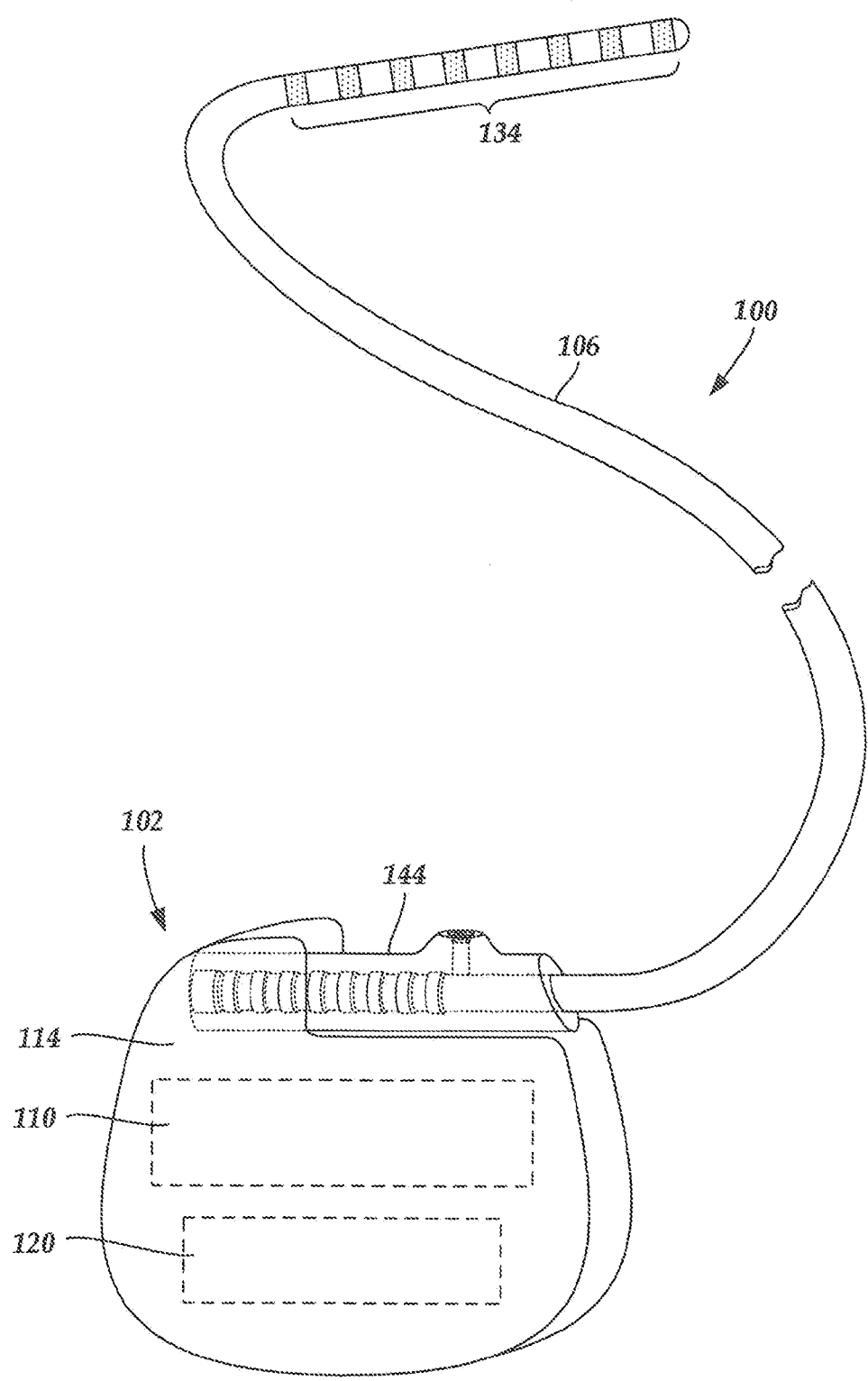
FIG. 2 is a schematic view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. The control module 102 typically includes a connector 144 (FIGS. 2 and 3A, see also 322 and 350 of FIG. 3B) into which the proximal end of the one or more lead bodies 106 can be plugged to make an electrical connection via conductive contacts on the control module 102 and terminals (e.g., 310 in FIG. 3A and 336 of FIG. 3B) on each of the one or more lead bodies 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 312 (see FIG. 3B) can be disposed between the one or more lead bodies 106 and the control module 102 to extend the distance between the one or more lead bodies 106 and the control module 102 of the embodiments shown in FIGS. 1 and 2.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or one or more lead bodies 106 are typically disposed in, or separated by, a non-conductive, biocompatible material including, for example, silicone, polyurethane, polyetheretherketone ("PEEK"), epoxy, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A and 336 of FIG. 3B) are typically disposed at the proximal end of the one or more lead bodies 106 for connection to corresponding conductive contacts (e.g., 314 in FIG. 3A and 340 of FIG. 3B) in connectors (e.g., 144 in FIGS. 1-3A and 322 and 350 of FIG. 3B) disposed on, for example, the control module 102 (or to other devices, such as conductive contacts on a lead extension, an operating room cable, or an adaptor). Conductive wires ("conductors") (not shown) extend from the terminals (e.g., 310 in FIG. 3A and 336 of FIG. 3B) to the electrodes 134. Typically, one or more electrodes 134 are electrically coupled to a terminal (e.g., 310 in FIG. 3A and 336 of FIG. 3B). In some embodiments, each terminal (e.g., 310 in FIG. 3A and 336 of FIG. 3B) is only connected to one electrode 134. The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

Figure 3A:
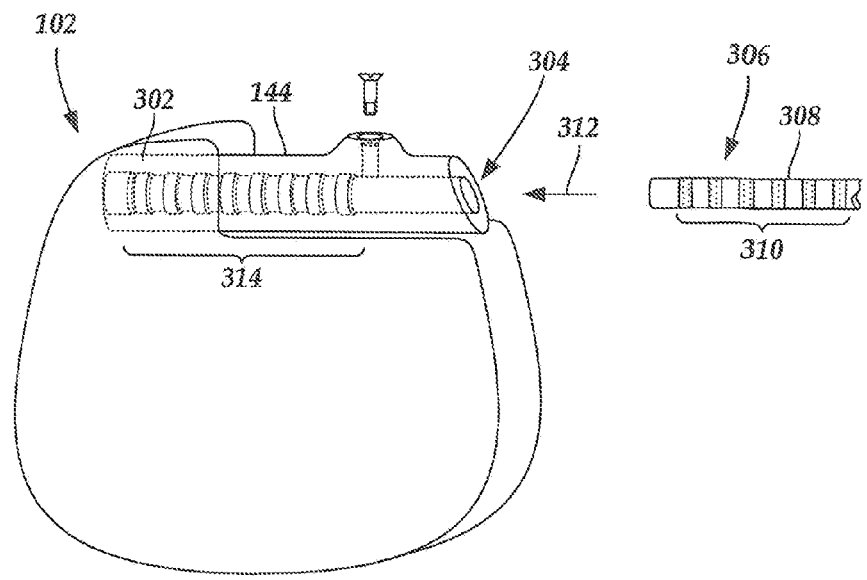
FIG. 3A is a schematic view of one embodiment of a proximal portion of a lead and a control module of an electrical stimulation system, according to the invention.

In at least some embodiments, leads are coupled to connectors disposed on control modules. In FIG. 3A, a lead 308 is shown configured and arranged for insertion to the control module 102. The connector 144 includes a connector housing 302. The connector housing 302 defines at least one port 304 into which a proximal end 306 of a lead 308 with terminals 310 can be inserted, as shown by directional arrow 312. The connector housing 302 also includes a plurality of conductive contacts 314 for each port 304. When the lead 308 is inserted into the port 304, the conductive contacts 314 can be aligned with the terminals 310 on the lead 308 to electrically couple the control module 102 to the electrodes (134 of FIG. 1) disposed at a distal end of the lead 308. Examples of connectors in control modules are found in, for example, U.S. Pat. Nos. 7,244,150 and 8,224,450, which are incorporated by reference.

Figure 3B:
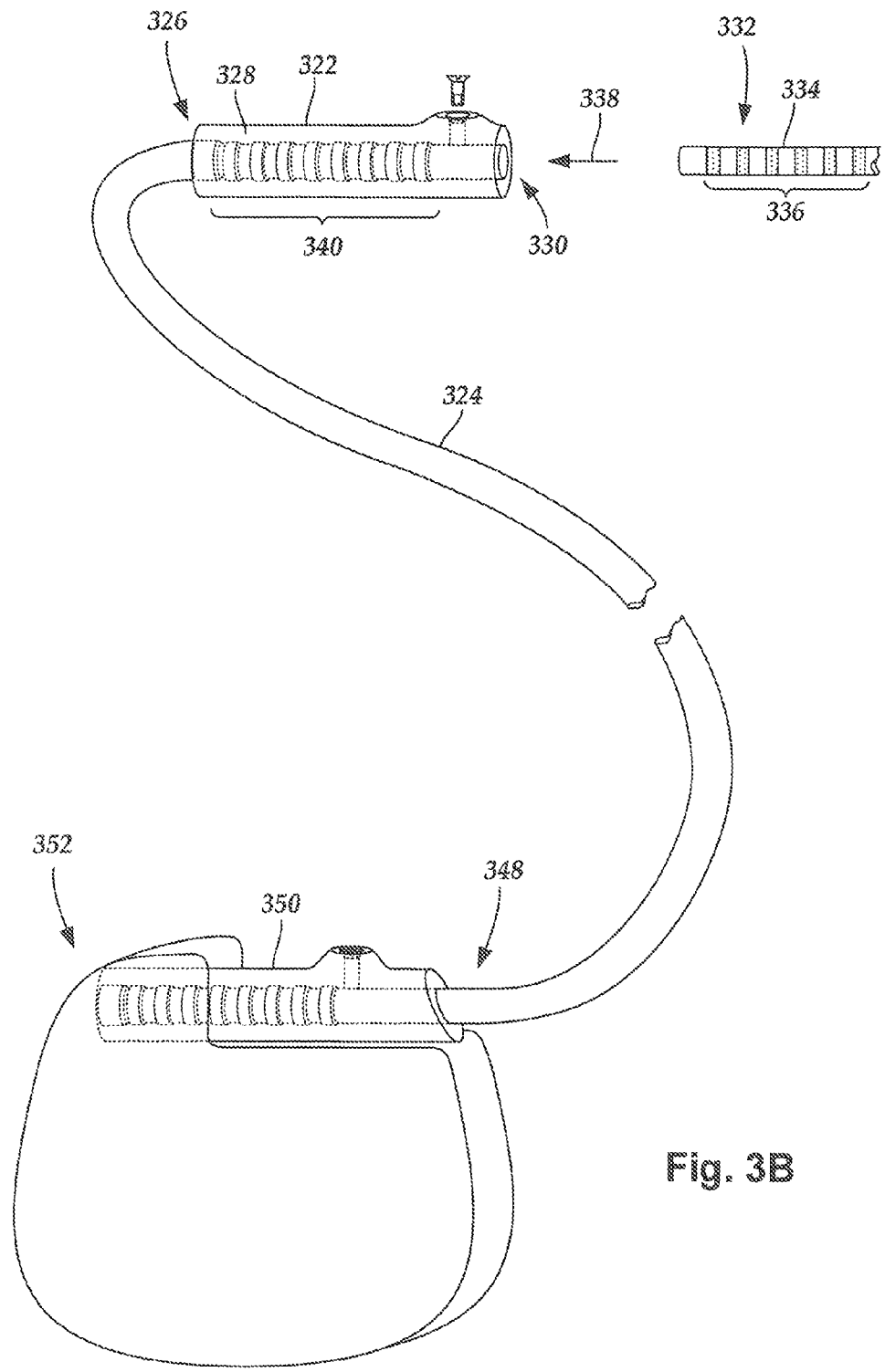
FIG. 3B is a schematic view of one embodiment of a proximal portion of a lead and a lead extension of an electrical stimulation system, according to the invention.

In FIG. 3B, a connector 322 is disposed on a lead extension 324. The connector 322 is shown disposed at a distal end 326 of the lead extension 324. The connector 322 includes a connector housing 328. The connector housing 328 defines at least one port 330 into which a proximal end 332 of a lead 334 with terminals 336 can be inserted, as shown by directional arrow 338. The connector housing 328 also includes a plurality of conductive contacts 340. When the lead 334 is inserted into the port 330, the conductive contacts 340 disposed in the connector housing 328 can be aligned with the terminals 336 on the lead 334 to electrically couple the lead extension 324 to the electrodes (134 of FIG. 1) disposed at a distal end (not shown) of the lead 334.

In at least some embodiments, the proximal end of a lead extension is similarly configured and arranged as a proximal end of a lead. The lead extension 324 may include a plurality of conductive wires (not shown) that electrically couple the conductive contacts 340 to a proximal end 348 of the lead extension 324 that is opposite to the distal end 326. In at least some embodiments, the conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a connector disposed in another lead extension. In other embodiments, the proximal end 348 of the lead extension 324 is configured and arranged for insertion into a connector disposed in a control module. As an example, in FIG. 3B the proximal end 348 of the lead extension 324 is inserted into a connector 350 disposed in a control module 352.

One or more of the conductors connecting at least one terminal to an electrode (or other conductive contact) can be arranged in a conductor path to eliminate or reduce the effect of RF irradiation, such as that generated during magnetic resonance imaging ("MRI"). The conductor path includes a plurality of units arranged in series. In some embodiments, the units are disposed along a single continuous conductor. In other embodiments, the units are separate conductive elements electrically coupled together.

Each unit includes at least three conductor segments that at least partially overlap one another to form a multi-coil region. First, each unit includes a first conductor segment that extends in a first direction along a longitudinal length of an elongated member (e.g., a lead or lead extension) from a beginning point to a first position. Second, each unit includes a second conductor segment that extends from the first position back towards (and possibly past) the beginning point to a second position. Third, each unit includes a third conductor segment that extends in the first direction from the second position to an endpoint. In at least some embodiments, the first position is between the second position and the endpoint. In at least some embodiments, the second position is between the beginning point and the first position. In at least some embodiments, the unit may include a single-coil region flanking at least one end of the multi-coil region.

The units may be electrically continuous such that the endpoint of a first unit is the beginning point of the next consecutive unit. At least one of the beginning points may be a terminal or an electrode (or other conductive contact). Likewise, at least one of the endpoints may be a terminal or an electrode (or other conductive contact). In preferred embodiments, the conductor segments are each coiled. In at least some embodiments, the conductor segments are coiled around a conductor placement sleeve. In at least some embodiments, the conductor placement sleeve defines a lumen that optionally is configured and arranged to receive a stiffening member (e.g., a stylet, or the like).

In at least some embodiments, at least one of the first, second, or third conductor segments is substantially straight. In at least some embodiments, the first and third conductor segments are substantially straight and the second conductor segment is coiled. In at least some other embodiments, all three conductor segments are substantially straight. It will be understood that the term "substantially straight conductor segment" means that the conductor segment is not coiled. A "substantially straight conductor segment" may be curved, particularly when the lead itself is curved (see, for example, FIG. 1).

In at least some embodiments, the conductor segments are all formed from the same length of conductive material (e.g., wire or the like). The conductors may have a single filament or be multi-filar. In preferred embodiments, the conductors are multi-filar. In at least some embodiments, two or more of the conductor segments can be individual pieces of conductive material that are electrically coupled (e.g., soldered or welded) together. In preferred embodiments, a layer of insulation ("conductor insulation") is disposed over each of the conductor segments.

In at least some embodiments, the length of conductor used in the second conductor segment is at least 1.5, 1.75, 1.9, 2, 2.1, 2.25, or 2.5 times the length of either the first conductor segment or the third conductor segment. It will be recognized, however, that this ratio of conductor-segment lengths may vary among embodiments, particularly if the thickness of the conductor or thickness of the layer of conductor insulation is different for the different segments.

Figure 4:
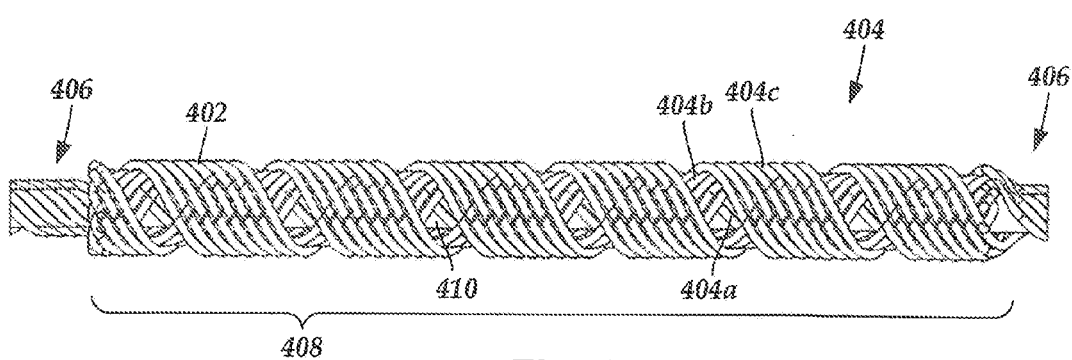
FIG. 4 is a schematic side view of one embodiment of portions of a plurality of conductors disposed along a conductor placement sleeve, the conductors configured into units, according to the invention.

FIG. 4 schematically illustrates one embodiment of a plurality of conductors 402. The conductors 402 are configured into a plurality of units, such as unit 404. Each unit includes a first conductor segment 404a, a second conductor segment 404b, and a third conductor segment 404c. In at least some embodiments, conductor insulation is disposed over the conductors 402 to electrically isolate each of the conductors 402 from one another.

Many different numbers of units may be disposed along longitudinal lengths of the conductors 402 including, for example, two, three, four, five, six, seven, eight, nine, ten, twelve, fifteen, twenty, twenty-five, thirty, forty, fifty, or more units. It will be understood that many other numbers of units may be employed as well. When a plurality of units are coupled together in series along a longitudinal length of one or more conductors, the plurality of units form a repeating series of single-coil regions, such as the single-coil regions 406, separated from one another by a multi-coil region, such as the multi-coil region 408.

In at least some embodiments, the conductors 402 are disposed along a conductor placement sleeve 410. The conductor placement sleeve 410 can be formed from any suitable biocompatible material including, for example, one or more polymers.

In at least some embodiments, one or more conductors having one or more units may be disposed in an elongated member (e.g., a lead or lead extension). In at least some embodiments, the ends of the conductors 402 can be coupled to terminals, electrodes, or conductive contacts. In preferred embodiments, each of the conductors in an elongated member are configured into units. In at least some embodiments, only a subset of the conductors disposed in an elongated member include one or more units, the remaining conductors having a different arrangement (for example, a single conductor segment between the terminal(s) and electrode(s)/conductive contact(s)).

Figure 5:
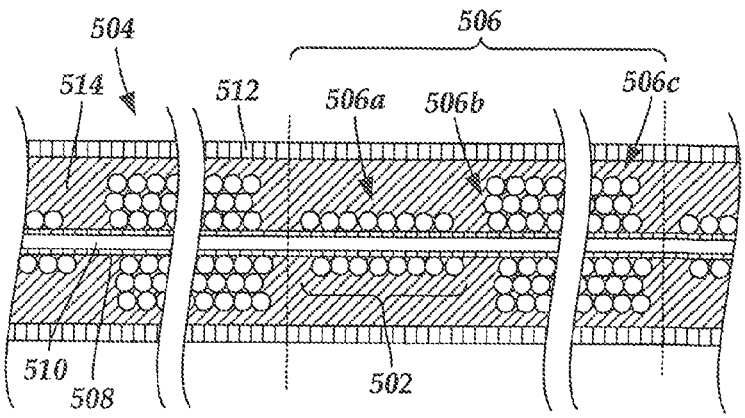
FIG. 5 is a schematic longitudinal cross-sectional view of one embodiment of portions of a plurality of conductors disposed in an elongated member, according to the invention.

Conductors, such as the conductors 402, may be disposed in a lumen of an elongated member (e.g., a lead, lead extension, or the like). In at least some embodiments, the conductors 402 are insulated. FIG. 5 is a schematic longitudinal cross-sectional view of one embodiment of portions of a plurality of conductors 502 disposed in an elongated member 504. The illustrated portions of the conductors 502 includes unit 506, shown between two vertical dotted lines. Unit 506 includes a first conductor segment 506a, a second conductor segment 506b, and a third conductor segment 506c. In at least some embodiments, the conductors 502 are disposed over a conductor placement sleeve 508. In at least some embodiments, the conductor placement sleeve 508 defines a lumen 510. The elongated member 504 includes a body 512 and a lumen 514 into which the conductors 502 are disposed.

Figure 6A:
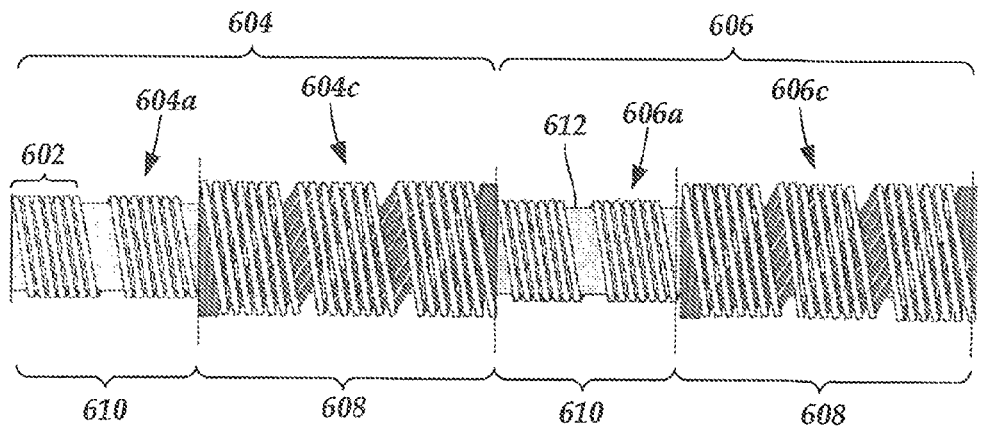
FIG. 6A is a schematic side view of one embodiment of a plurality of portions of conductors formed into two units that include alternating single-coil regions and multi-coil regions, according to the invention.

FIG. 6A schematically illustrates a side view of one embodiment of a plurality of conductors 602 each including units 604 and 606. In FIG. 6A, the first, second, and third conductor segments 604a, 604b (not shown in FIG. 6A), and 604c, respectively, of the unit 604, and the first, second, and third conductor segments 606a, 606b (not shown in FIG. 6A) and 606c, respectively, of the unit 606, are each coiled. The conductors 602 are arranged such that the conductors include multi-coil regions 608 and single-coil regions 610. In at least some embodiments, the conductors 602 may be coiled around one or more objects, such as a conductor placement sleeve 612.

Figure 6B:
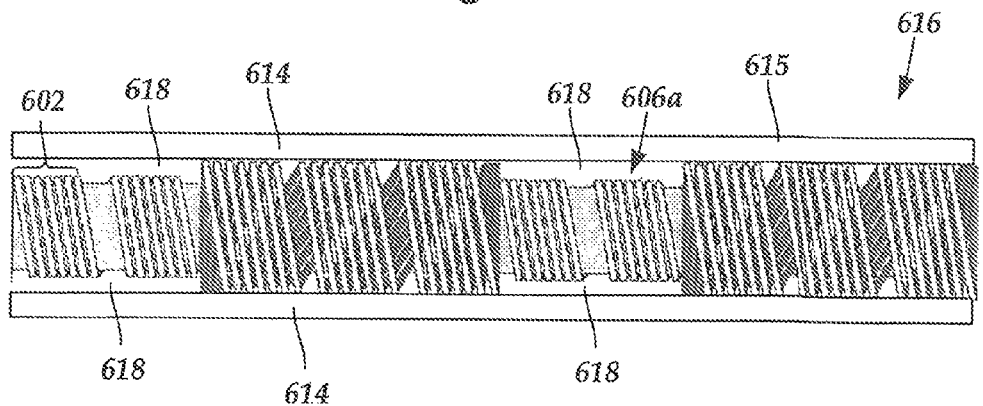
FIG. 6B is a schematic side view of one embodiment of the portions of conductors of FIG. 6A with a longitudinal cross-sectional view of an outer layer disposed over the portions of conductors, according to the invention.

FIG. 6B is a schematic longitudinal cross-sectional view of the plurality of conductors 602 disposed in an outer layer 614 of a body 615 of a lead 616. When the outer layer 614 of the body 615 is isodiametric along the longitudinal length of the lead 616, open spaces 618 may form between the single-coil regions, such as single-coil region 606a, and the outer layer 614.

As discussed above, exposure of an implanted electrical stimulation system to RF irradiation (e.g., during an MRI procedure) may cause harm to the patient. In at least some embodiments, a safety element is disposed in an elongated member for reducing one or more deleterious effects caused by exposure to RF irradiation, such as unwanted heating of patient tissue or undesired induced electrical signals.

In at least some embodiments, the safety element alters one or more responses of the elongated member to exposure to RF irradiation. In some embodiments, the safety element reduces heat build-up by actively or passively altering heat conduction within the elongated member. In other embodiments, the safety element reduces undesired induced electrical signals by shunting the undesired induced electrical signals away from patient tissues or by reducing the ability of the elongated member to convert RF irradiation to induced electrical signals.

In at least some embodiments, the safety element is incorporated into a stylet that remains disposed in one or more lumens defined in the elongated member after the elongated member is implanted. In at least some embodiments, the stylet is the same stylet that is used to guide the elongated member to the target site during implantation. In at least some other embodiments, the safety element is separate from the stylet and is inserted into one or more of the lumens after the elongated member has been guided to the target site and the stylet has been removed. In at least some other embodiments, the safety element is disposed along one or more non-lumen portions of the body of the elongated member. In at least some embodiments, the safety element may be disposed external to the body of the elongated member.

Figure 7A:
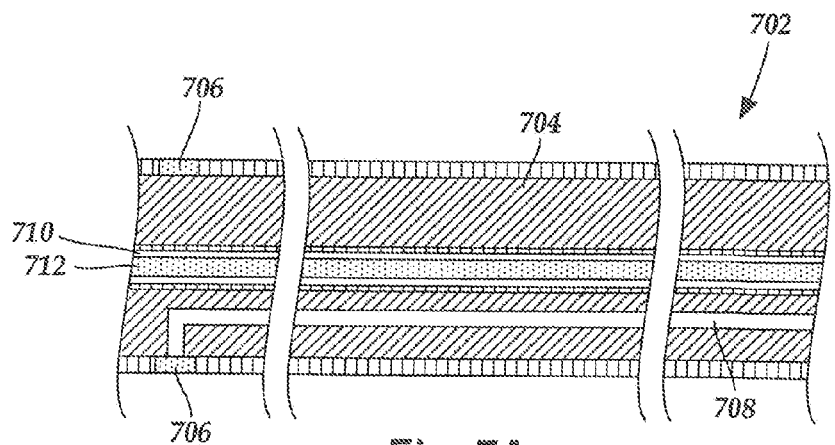
FIG. 7A is a schematic longitudinal cross-sectional view of one embodiment of a portion of an elongated member that includes a conductor coupled to an electrode, the elongated member also defining a lumen in which a safety element is disposed, according to the invention.

In at least some embodiments, the safety element is disposed in a lumen defined in the elongated member. FIG. 7A is a schematic longitudinal cross-sectional view of one embodiment of a portion of an elongated member (e.g., a lead or lead extension) 702. The elongated member 702 includes a body 704. An electrode 706 is disposed along an outer layer of the body 704. A conductor 708 is disposed in the body 704 and electrically couples the electrode 706 to a terminal disposed at a proximal end of the elongated member 702. A lumen 710 is defined along at least a portion of the elongated member 702. A safety element 712 is disposed along at least a portion of the lumen 710.

Figure 7B:
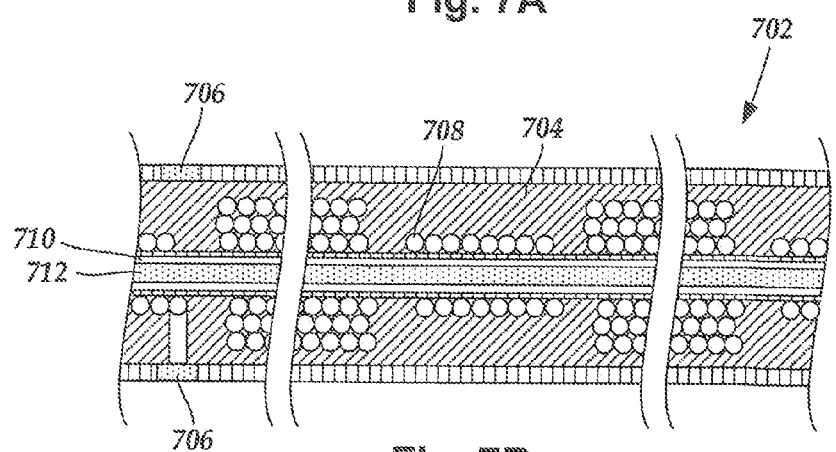
FIG. 7B is a schematic longitudinal cross-sectional view of one embodiment of a portion of an elongated member that includes a conductor formed into units and coupled to an electrode, the elongated member also defining a lumen in which a safety element is disposed, according to the invention.

Typically, a plurality of conductors extend along the length of the elongated member 702. Only a single conductor 708 is shown in FIG. 7A, and in subsequent figures, as a single conductor, for clarity of illustration. It will be understood that, when a plurality of conductors are disposed in the elongated member 702, one or more of the conductors may extend in one or more different configurations. FIG. 7B is a schematic longitudinal cross-sectional view of another embodiment of the conductor 708 arranged into units and extending along the length of the elongated member 702.

In at least some embodiment, the safety element 712 reduces heat build-up by passively altering heat conduction within the elongated member 704. In at least some embodiments, the safety element 712 draws heat away from outer surfaces of the elongated member 702 (e.g., the body 704) to the lumen 710. In at least some embodiments, the safety element 712 has a heat capacity that is at least as great as the body 704. In at least some other embodiments, the safety element 712 has a heat capacity that is substantially greater than the body 704. In some embodiments, the safety element 712 distributes heat along substantially the entire longitudinal length of the lumen 710 of the elongated member 702. In some embodiments, the safety element 712 additionally distributes heat to at least a portion of the control module (102 in FIG. 1) or the lead extension (324 in FIG. 3B), when applicable. In at least some embodiments, heat is transferred from the body 704 to the safety element 712 either directly or radiantly.

The heat dissipating safety element 712 may be formed with any heat dissipating material suitable for implantation into a patient including, for example, solids (e.g., metals, alloys, polymers, carbon, composite materials, or the like) or fluids (e.g., saline solution, water, or the like). In at least some embodiments, the safety element 712 is a heat sink. In at least some embodiments, the safety element 712 includes a plurality of protrusions (not shown) extending along at least a portion of the length of the safety element 712 for increasing the surface area of the safety element 712.

Figure 8:
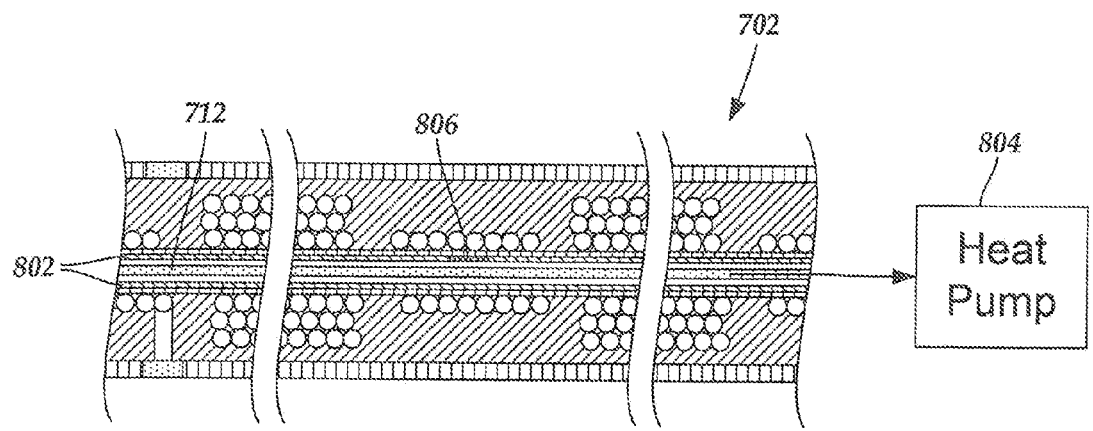
FIG. 8 is a schematic longitudinal cross-sectional view of one embodiment of a portion of a cooling device disposed on the safety element of FIG. 7B, according to the invention.

In at least some embodiment, the safety element 712 reduces heat build-up by actively altering heat conduction within the elongated member 704. FIG. 8 is a schematic longitudinal cross-sectional view of one embodiment of a cooling device 802 disposed on the safety element 712. In at least some embodiments, the cooling device 802 can be employed to actively cool at least a portion of the elongated member 702 for some period of time. In at least some embodiments, the safety element 712 employs thermoelectric cooling, wherein a heat flux is formed at the interface between the safety element 712 and the body 704. In at least some embodiments, an active heat pump (e.g., a Peltier cooler) 804 is employed to transfer heat from the body 704, via the safety element 712, against a temperature gradient. The heat pump 804 may be positioned anywhere within the electrical stimulation system or as a separate, stand-alone unit. Typically, it is preferred to position the heat pump 804 in proximity to the heating or in a location in the body that can efficiently couple heat from the device. In at least some embodiments, the heat pump 804 receives power from the control module (102 in FIG. 1), as shown schematically in FIG. 11. In at least some embodiments a fluid circulation device may be used as a cooling device.

In at least some embodiments, the cooling device 802 may be activated using an activator (e.g., a switch, button, knob, or the like) disposed on the control module (102 in FIG. 1) and accessible through patient tissue, or by using a remote control. In at least some embodiments, the electrical stimulation system includes a sensor 806 that activates the cooling device 804 when the sensor 806 senses RF irradiation, a magnetic field, or both at or above a threshold value or within a certain frequency range. Many different types of sensors may be employed including, for example, a reed switch, a Hall-effect switch, or the like. In FIG. 8 the sensor 806 is shown disposed on the safety element 712. It will be understood that the sensor 806 may be disposed anywhere on the electrical stimulation system.

In at least some embodiments, the cooling device activates in response to a temperature at or above a threshold temperature. In at least some embodiments, the cooling device 802 is adjustable such that the cooling device 802 increases in strength when the sensed temperature increases above other threshold values that are higher than the activation threshold values. In at least some embodiments, the safety element 712 employs a feedback loop, during operation, to adjust the cooling power of the cooling device 802 in response to changes in temperature.

As discussed above, some electrical signals transmitting along the electrode 706 and the conductor 708 are desirable (e.g., electrical stimulation via the pulse generator of the control module (102 in FIG. 1)). Some applied electrical signals, however, may be undesirable (e.g., electrical signals induced via exposure to RF irradiation, for example, during an MRI procedure). In at least some embodiments, undesired electrical signals may be shunted away from patient tissue via the safety element 712. In at least some embodiments, the ability of the elongated member 702 to shunt electrical signals may vary based on one or more characteristics of the electrical signal or based on sensing one or more environmental conditions (e.g., sensing RF irradiation above a threshold level). In at least some embodiments, undesired electrical signals received by the elongated member 702 may be reduced by reducing the ability of the elongated member 702 to convert RF irradiation to an induced electrical signal within the elongated member 702 (i.e., altering the antenna characteristics of the elongated member 702).

In at least some embodiments, at least one of the electrode 706 or the conductor 708 may be electrically coupled to the safety element 712 for shunting undesired electrical signals away from patient tissue, while not shunting desired electrical signals under normal operating conditions. In at least some embodiments, at least one of the terminals (e.g., terminal 400 in FIGS. 4A-4B) may be electrically coupled to the safety element 712 for shunting undesired electrical signals away from patient tissue, while not shunting desired electrical signals under normal operating conditions.

Figure 9A:
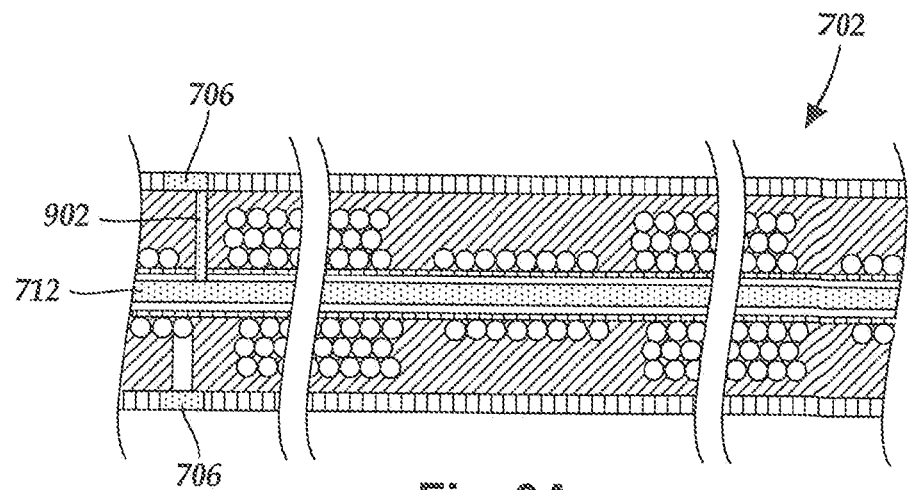
FIG. 9A is a schematic longitudinal cross-sectional view of one embodiment of an electrode shunt coupling the electrode of FIG. 7B to the safety element of FIG. 7B, according to the invention.

In at least some embodiments, the safety element 712 may be coupled to the electrode 706. FIG. 9A is a schematic longitudinal cross-sectional view of one embodiment of at least one electrode shunt 902 coupling the electrode 706 to the safety element 712. It will be understood that there may be a plurality of electrodes 706 disposed at the distal end of the elongated member 702. In which case, there may be a plurality of electrode shunts 902 coupling the electrodes 706 to the safety element 712. It will be understood that, when the elongated member 702 is a lead extension, one or more conductor-contact shunts may also be employed to couple one or more connector contacts (see e.g., 340 in FIG. 3B) to the safety element 712.

Figure 9B:
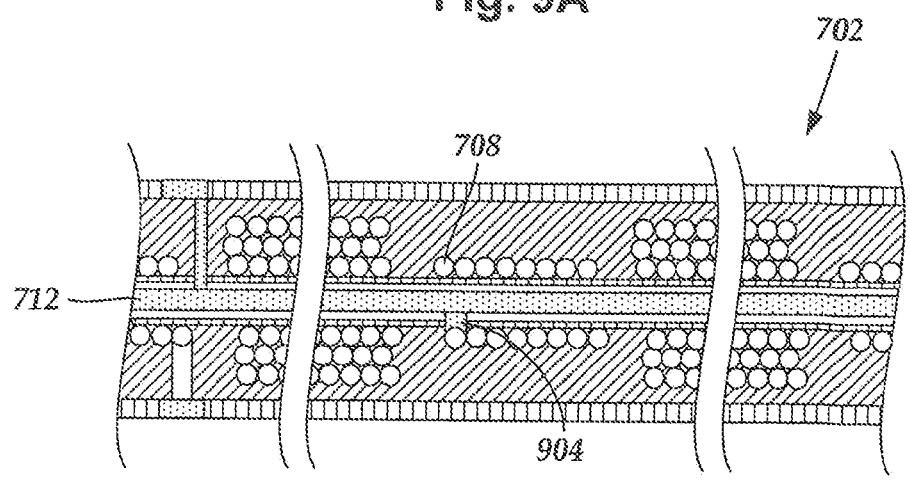
FIG. 9B is a schematic longitudinal cross-sectional view of one embodiment of a conductor shunt coupling the conductor of FIG. 7B to the safety element of FIG. 7B, according to the invention.

FIG. 9B is a schematic longitudinal cross-sectional view of one embodiment of at least one conductor shunt 904 coupling the conductor 708 to the safety element 712. It will be understood that there may be a plurality of conductors 708 disposed along the longitudinal length of the elongated member 702. In which case, there may be at least one conductor shunt 904 coupling each of a plurality of the conductors 708 to the safety element 712.

The shunts 902 and 904 may include any number of different types of connections including, for example, direct electrical connection by a filter (e.g., a high-pass filter, a low-pass filter, a bandpass filter, or the like) coupled to one or more conductors, one or more capacitors, one or more inductors, or the like. When a direct electrical connection is employed, the shunts 902 and 904 may be formed from any conductive material suitable for implantation into a patient.

In at least some embodiments, undesired electrical signals (e.g., RF irradiation from an MRI procedure) may be shunted to portions of the elongated body 402 not directly contacting the patient. In at least some embodiments, at least some of the undesired electrical signals are shunted to the safety element 712 from the electrode 706 or the conductor 708 via the shunts 902 or 904, respectively. In at least some embodiments, at least some of the undesired electrical signals are shunted to the control module (102 in FIG. 1), or the lead extension (324 in FIG. 3B), if applicable, for dissipation over a larger region of the body.

In at least some embodiments, conduction of electrical signals via one or more of the shunts 902 or 904 may vary based on one or more characteristics of the electrical signal or based on the sensing of one or more environmental conditions. Thus, it is preferred that undesired electrical signals are shunted to the safety element 712 and desired electrical signals are not.

In at least some embodiments, the shunting ability of the one or more shunts 902 or 904 is based on the frequency of the electrical signal. For example, in at least some embodiments, one or more filters (e.g. high-pass filters, low-pass filters, bandpass filters, or the like) are employed so that the shunts 902 or 904 have high impedance (i.e., an open circuit) to electrical signals with frequencies at or below (or within) a threshold level, thereby allowing the electrical signals to transmit freely along the conductor 708 and the electrode 706 without being shunted to the safety element 712. In at least some embodiments, the shunts 902 or 904 have a high impedance when applied electrical signals have frequencies no greater than 1 MHz. In at least some embodiments, the shunts 902 or 904 have a high impedance when applied electrical signals have frequencies no greater than 2 MHz. In at least some embodiments, the shunts 902 or 904 have a high impedance when applied electrical signals have frequencies no greater than 5 MHz.

In at least some embodiments, the shunts 902 or 904 have low impedance (i.e., a closed circuit) to electrical signals with frequencies at or above a threshold value, thereby shunting the electrical signals to the safety device 712. In at least some embodiments, the shunts 902 or 904 may have low impedance when electrical signals have frequencies no less than 8 MHz. In at least some embodiments, the shunts 902 or 904 may have low impedance when electrical signals have frequencies no less than 9 MHz. In at least some embodiments, the shunts 902 or 904 may have low impedance when electrical signals have frequencies no less than 10 MHz. In at least some embodiments, the shunts 902 or 904 may have low impedance when electrical signals have frequencies no less than 11 MHz.

It will be understood that the shunts 902 or 904 may, instead, have low or high impedance to electrical signals with frequency ranges. It will also be understood that the shunting ability of the shunts 902 or 904 may be based on other characteristics of the signal (e.g., the amplitude of the signal, the duration of the signal, or the like) or one or more environmental conditions (e.g., sensing RF irradiation or a magnetic field above a threshold level). In at least some embodiments, a sensor (see e.g., sensor 806 in FIG. 8) is incorporated into the electrical stimulation system to sense RF irradiation.

In at least some embodiments, the safety element 712 alters the antenna characteristic of the elongated member 702. For example, in at least some embodiments, the materials and arrangements used to form the safety element 712 may be selected such that the elongated member 702 has a reduced ability to convert RF irradiation to an induced electrical signal (i.e., the elongated member 702 becomes a poor antenna) within one or more undesirable frequency ranges, such as frequency ranges commonly used during MRI procedures.

Figure 10:
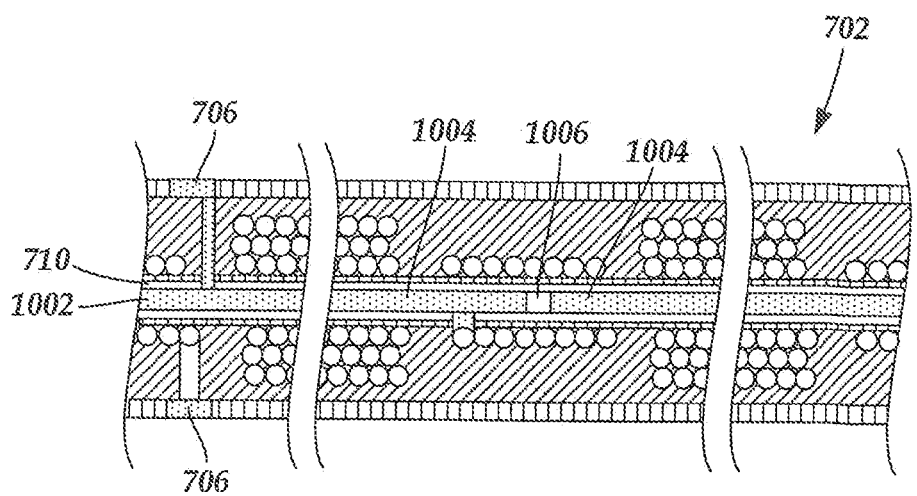
FIG. 10 is a schematic longitudinal view of one embodiment of a safety element with a plurality of sections disposed in the elongated body of FIG. 7B.

FIG. 10 is a schematic longitudinal cross-sectional view of one embodiment of a safety element 1002 disposed in the lumen 710 of the elongated member 702. The safety element 1002 includes a plurality of sections of conductive materials 1004 separated from one another by non-conductive connecting material 1006. The antenna characteristics of the elongated member 702 (e.g., the self-resonant frequency, lossiness, frequency-dependent behavior at the frequencies of interest, or the like or combinations thereof) may be affected by one or more of the characteristics of the safety element 1002 including, for example, the permittivity or the conductivity of the safety element 1002. Many different materials may be used to form the conductive sections 1004 including, for example, metals (e.g., platinum, silver, or the like or combinations thereof), an electrolyte solution (e.g., a saline solution, or the like), one or more polymers or other conductive elements (e.g., one or more polymers embedded with conductive beads), or the like or combinations thereof.

In at least some embodiments, a plurality of safety elements may be employed with the elongated member. In at least some embodiments, when a plurality of safety elements are employed, two or more of the safety elements may be coupled to one another. In at least some embodiments, the elongated member defines a plurality of lumens. In at least some embodiments, one or more safety elements are disposed in a single lumen. In at least some other embodiments, one or more safety elements are disposed in multiple lumens. In at least some embodiments, a single safety element is disposed in a plurality of lumens.

In at least some embodiments, at least a portion of the safety element is injected into the lumen. In at least some embodiments, at least a portion of the safety element flows when applied to the lumen. In at least some embodiments, at least a portion of the safety element gels, sets, or cross-links subsequent to application.

Figure 11:
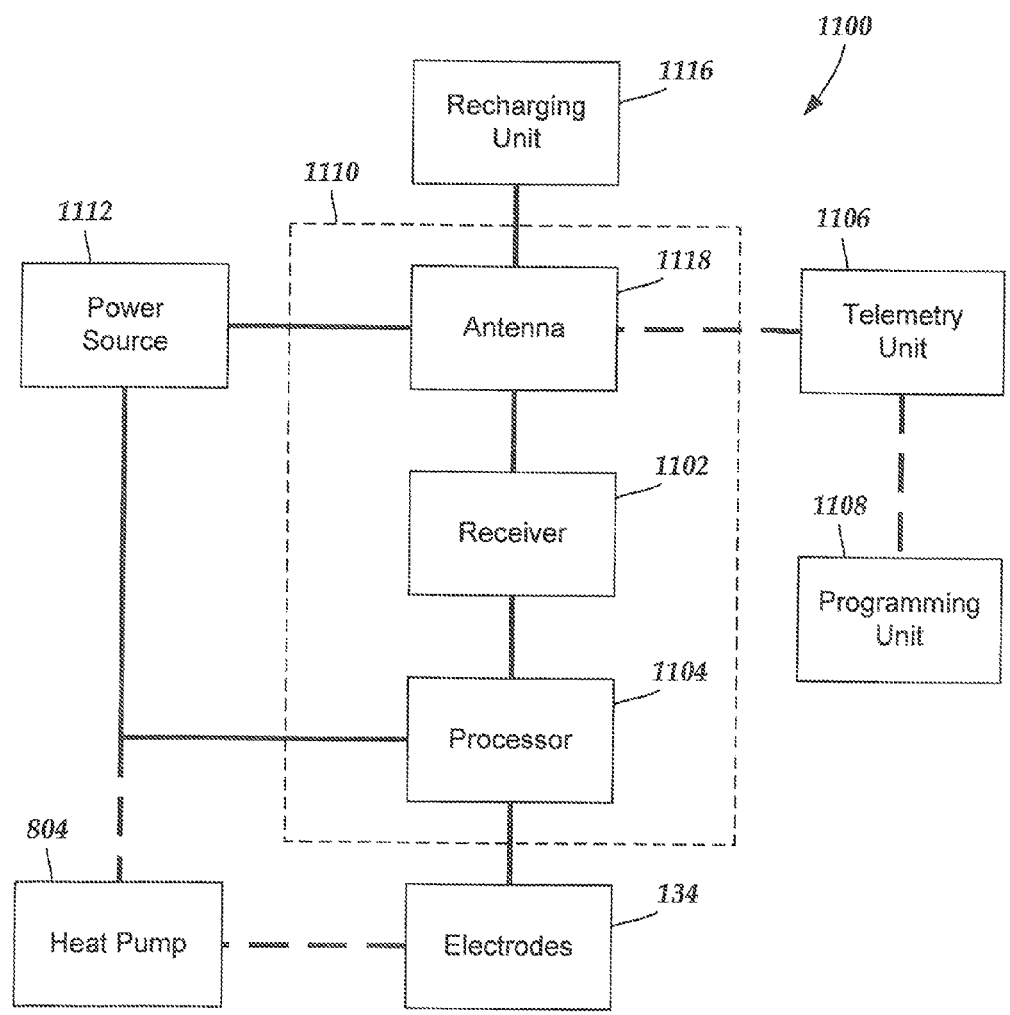
FIG. 11 is a schematic overview of one embodiment of components of a stimulation system, including an electronic subassembly disposed within a control module, according to the invention.

FIG. 11 is a schematic overview of one embodiment of components of an electrical stimulation system 1100 including an electronic subassembly 1110 disposed within a control module. It will be understood that the electrical stimulation system can include more, fewer, or different components and can have a variety of different configurations including those configurations disclosed in the stimulator references cited herein.

Some of the components (for example, power source 1112, antenna 1118, receiver 1102, and processor 1104) of the electrical stimulation system can be positioned on one or more circuit boards or similar carriers within a sealed housing of an implantable pulse generator, if desired. Any power source 1112 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1118 or a secondary antenna. The external power source can be in a device that is mounted on the skin of the user or in a unit that is provided near the user on a permanent or periodic basis.

If the power source 1112 is a rechargeable battery, the battery may be recharged using the optional antenna 1118, if desired. Power can be provided to the battery for recharging by inductively coupling the battery through the antenna to a recharging unit 1116 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1104 is generally included to control the timing and electrical characteristics of the electrical stimulation system. For example, the processor 1104 can, if desired, control one or more of the timing, frequency, strength, duration, and waveform of the pulses. In addition, the processor 1104 can select which electrodes can be used to provide stimulation, if desired. In some embodiments, the processor 1104 may select which electrode(s) are cathodes and which electrode(s) are anodes. In some embodiments, the processor 1104 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1108 that, for example, allows modification of pulse characteristics. In the illustrated embodiment, the processor 1104 is coupled to a receiver 1102 which, in turn, is coupled to the optional antenna 1118. This allows the processor 1104 to receive instructions from an external source to, for example, direct the pulse characteristics and the selection of electrodes, if desired.

In one embodiment, the antenna 1118 is capable of receiving signals (e.g., RF signals) from an external telemetry unit 1106 which is programmed by a programming unit 1008. The programming unit 1108 can be external to, or part of, the telemetry unit 1106. The telemetry unit 1106 can be a device that is worn on the skin of the user or can be carried by the user and can have a form similar to a pager, cellular phone, or remote control, if desired. As another alternative, the telemetry unit 1106 may not be worn or carried by the user but may only be available at a home station or at a clinician's office. The programming unit 1108 can be any unit that can provide information to the telemetry unit 1106 for transmission to the electrical stimulation system 1100. The programming unit 1108 can be part of the telemetry unit 1106 or can provide signals or information to the telemetry unit 1106 via a wireless or wired connection. One example of a suitable programming unit is a computer operated by the user or clinician to send signals to the telemetry unit 1106.

The signals sent to the processor 1104 via the antenna 1118 and receiver 1102 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1100 to cease operation, to start operation, to start charging the battery, or to stop charging the battery. In other embodiments, the stimulation system does not include an antenna 1118 or receiver 1102 and the processor 1104 operates as programmed.

Optionally, the electrical stimulation system 1100 may include a transmitter (not shown) coupled to the processor 1104 and the antenna 1118 for transmitting signals back to the telemetry unit 1106 or another unit capable of receiving the signals. For example, the electrical stimulation system 1100 may transmit signals indicating whether the electrical stimulation system 1100 is operating properly or not or indicating when the battery needs to be charged or the level of charge remaining in the battery. The processor 1104 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation lead assembly comprising:
   a lead configured and arranged for insertion into a body of a patient, the lead comprising
      a lead body having a distal end portion, a proximal end portion, an outer surface, and a longitudinal length,
      at least one lumen extending along the longitudinal length of the lead body, the at least one lumen configured and arranged to receive a stylet,
      a plurality of electrodes disposed along the distal end portion of the lead body external to the at least one lumen,
      a plurality of terminals disposed along the proximal end portion of the lead body external to the at least one lumen, and
      a plurality of conductors disposed in the lead body external to the at least one lumen, each conductor electrically coupling at least one of the plurality of electrodes to at least one of the plurality of terminals; and
   at least one safety element disposed in the at least one lumen, the at least one safety element configured and arranged to reduce damage to patient tissue adjacent to the lead body due to heating, induced electrical signals, or both when the lead is exposed to radio frequency irradiation by drawing heat inwardly from the outer surface of the lead body;
   wherein the at least one safety element is configured and arranged to draw heat inwardly from the outer surface of the lead body by actively altering heat conduction within the lead body.

2. The lead assembly of claim 1, wherein the at least one safely element comprises a cooling device configured and arranged for reducing the temperature of the lead.

3. The lead assembly of claim 2, wherein the cooling device comprises a heat pump configured and arranged for transferring heat from the lead body to the at least one safety element against a temperature gradient.

4. The lead assembly of claim 3, wherein the heat pump is configured and arranged to receive power from a control module coupled to the lead body.

5. The lead assembly of claim 1, wherein the at least one safety element is configured and arranged to draw heat from the outer surface of the lead body to the at least one lumen.

6. The lead assembly of claim 5, wherein the at least one safety element is configured and arranged to distribute heat drawn from the outer surface of the lead body along substantially an entire longitudinal length of the at least one lumen.

7. The lead assembly of claim 1, wherein the at least one safety element has a heat capacity that is substantially greater than a heat capacity of the lead body.

8. The lead assembly of claim 1, wherein the at least one safety element is formed as a solid.

9. The lead assembly of claim 8, wherein the at least one safety element comprises at least one of a metal, an alloy, a composite, or a polymer.

10. The lead assembly of claim 1, wherein the at least one safety element is formed as a fluid.

11. The lead assembly of claim 1, wherein at least one of the plurality of conductors is disposed in the lead body in a substantially-straight configuration.

12. The lead assembly of claim 1, wherein at least one of the plurality of conductors comprises a plurality of units, each unit comprising
    a first conductor segment extending along the lead body from a beginning point to a first position,
    a second conductor segment extending front the first position to a second position, and
    a third conductor segment extending along the elongated lumber from the second position to an endpoint,
wherein the conductor segments are arranged so as to form alternating single-coil regions and multi-coil regions.

13. An electrical stimulating system comprising:
    the lead assembly of claim 1;
    to control module configured and arranged to electrically couple to the proximal end of the lead body of the lead assembly, the control module comprising
        a housing, and
        an electronic subassembly disposed in the housing; and
    a connector for receiving the lead body, the connector having a proximal end portion and a distal end portion, the connector comprising
        a connector housing defining a port along the distal end portion of the connector, the port configured and arranged for receiving the proximal end portion of the lead body, and
        a plurality of connector contacts disposed in the connector housing the connector contacts configured and arranged to couple to at least one of the plurality of terminals disposed on the proximal end portion of the lead body.

14. The electrical stimulating system of claim 13, further comprising a lead extension having a proximal end portion and a distal end portion, the connector disposed on the distal end portion of the lead extension.

15. The electrical stimulating system of claim 14, wherein the proximal end portion of the lead extension is configured and arranged for insertion into another connector.

16. The electrical stimulating system of claim 14, wherein the at least one safety element is configured and arranged to distribute heat drawn from the outer surface of the lead body to at least a portion of the lead extension.

17. The electrical stimulating system of claim 13, wherein the connector is disposed on the control module.

18. The electrical stimulating system of claim 13, wherein the at least one safety element is configured and arranged to distribute heat drawn from the outer surface of the lead body to a least a portion of the control module.

\* \* \* \* \*